United States Patent [19]

Haase et al.

[11] 4,158,035

[45] Jun. 12, 1979

[54] MULTIPLE SAMPLE MICROPIPETTE

[76] Inventors: Thomas Haase, 2996 Alta Laguna, Laguna Beach, Calif. 92651; William J. Byrd, 530 Kingsland Ave., Nutley, N.J. 07110

[21] Appl. No.: 886,569

[22] Filed: Mar. 15, 1978

[51] Int. Cl.$^2$ .......................... B01L 3/02; G01N 1/14
[52] U.S. Cl. .................................... 422/100; 73/425.6; 222/263; 141/25; 141/26; 141/27
[58] Field of Search ..................... 73/425.6, 425.4 P; 222/263; 141/25, 26, 27; 23/259; 422/100

[56] References Cited

U.S. PATENT DOCUMENTS

| 2,595,493 | 5/1952 | Slaby et al. | 73/425.6 |
|---|---|---|---|
| 3,568,735 | 3/1971 | Lancaster | 222/263 X |
| 3,572,552 | 3/1971 | Guinn | 73/425.6 X |
| 3,650,306 | 3/1972 | Lancaster | 222/263 |
| 3,807,235 | 4/1974 | Lefkovits et al. | 73/425.6 |
| 3,982,438 | 9/1976 | Byrd | 73/425.6 |

*Primary Examiner*—Michael S. Marcus
*Attorney, Agent, or Firm*—Gordon L. Peterson

[57] ABSTRACT

A pipetting device comprising a housing and a plurality of tubes mounted on the housing. The housing has a manifold chamber and a plurality of passages leading from the tubes, respectively, to the manifold chamber. A flexible impervious membrane extends across the passages to divide each of the passages into a first passage section and a second passage section. The first passage sections provide communication between the tubes and one side of the membrane, and the second passage sections provide communication from the other side of the membrane to the manifold chamber. A substantially incompressible flowable material, such as a liquid, fills the second passage sections and the manifold chamber. A mechanism is provided for moving the flowable material to deflect the membrane in opposite directions whereby liquid can be drawn into, and expelled from, the tubes.

8 Claims, 3 Drawing Figures

MULTIPLE SAMPLE MICROPIPETTE

BACKGROUND OF THE INVENTION

In various kinds of laboratory work, it is often necessary to transfer precise, small quantities of liquid from a first group of cavities to a second group of cavities. Such a need exists, for example, in microbiological and immunological laboratory work, as well as medical laboratory research.

This liquid transfer function is characteristically carried out with a pipetting device which includes a housing. The open ends of the tubes are placed into the first group of cavities and the pipetting device is coupled to a source of air at less than atmospheric pressure to thereby draw liquid into the tubes. The first group of cavities is then removed, and the tubes are placed into a second group of cavities. The vacuum pressure within the housing is then relieved to expel the liquid in the tubes into the second group of cavities.

The use of a pipetting concept to accomplish this liquid transfer is sound. Unfortunately, the devices developed heretofore for the purpose of carrying out this pipetting function possess several drawbacks. For example, the use of positive and negative air pressure to control the operation of the pipetting device, as exemplified by Lefkovitz U.S. Pat. No. 3,807,235 and Byrd U.S. Pat. No. 3,982,438, do not provide the accuracy required for laboratory work. In this regard, the volume of liquid transferred per cavity is typically in the microliter range and precise results are required.

In addition, the devices shown in the Lefkovitz and Byrd patents are capable of transferring only fixed volumes of liquid. For example, in order to alter liquid transfer volumes with the pipetting device shown in the Byrd patent, it is necessary to disassemble the device and replace one plate with another. This wastes time and increases the cost of the laboratory procedure.

The first and second group of cavities referred to hereinabove are characteristically provided in first and second trays, respectively, of standardized dimensions and having standard spacing between the cavities. As the ends of the tubes must be received in these cavities, the standardization of the trays controls the spacing between tubes. Typically, the center-to-center spacing of the cavities in the tray and hence of the tubes of the pipetting device is from seven to eight millimeters. Some liquid transfer operations require the transfer of 200 microliters of liquid per cavity. Because of the close center-to-center spacing of the tubes, the prior art pipetting devices do not provide adequate liquid transfer volumes.

SUMMARY OF THE INVENTION

This invention provides a pipetting device which generally overcomes the disadvantages noted above. For example, the pipetting device of this invention transfers liquid with greater accuracy than is possible with the prior art devices. In addition to greater accuracy, this invention also provides for the transfer of selectively variable liquid quantities without disassembly or modification of the pipetting device. Finally, the pipetting device of this invention can transfer up to 200 microliters of liquid per tube while maintaining a center-to-center tube spacing which is compatible with the standardized trays.

The concepts of this invention can be implemented with a pipetting device which comprises a housing and a plurality of tubes mounted on the housing. The housing has a manifold chamber and a plurality of passages leading from the tubes, respectively, to the manifold chamber. A flexible impervious membrane extends across the passages to divide each of the passages into first and second passage sections. The first passage sections provide communication, respectively, between the tubes and first locations on one side of the membrane, and the second passage sections extend respectively from second locations on the other side of the membrane to the manifold chamber. The first and second locations are on opposite sides of the membrane, respectively.

To make the pipetting device operate linearly and to improve the accuracy of the device, the second passage sections and the manifold chamber are filled with a substantially incompressible flowable material. By moving the flowable material, the membrane is deflected to draw in or expel liquid from the tubes.

The use of a substantially incompressible flowable material also facilitates selective adjustment of the volume of liquid transferred. This is accomplished by moving the flowable material a greater or lesser amount depending upon whether the volume to be transferred is to be increased or decreased. Because the flowable material is basically incompressible, a high degree of repeatability is obtained. With a compressible gas, the amount of liquid transferred varies with the elasticity of the flexible resilient membrane.

The flowable material can be moved or pumped in different ways. However, it is preferred to provide a cylinder in the manifold chamber and a movable piston in the cylinder. Means, such as a stepping motor, is provided for moving the piston to any one of a plurality of different positions in the cylinder. This controls and varies the deflection of the membrane means, as well as the amount of liquid transferred. Although the substantially incompressible flowable material could be a relatively thick extrubable material or a resiliently deformable mass of elastomeric material, preferably it is a liquid. For example, glycerin may be used.

The amount of fluid transferred depends upon the amount which the membrane is deflected by the flowable material. The amount which the membrane can deflect is in turn controlled in part by the configuration of the passage adjacent the membrane into which the membrane deflects. It is known to provide radial enlargements adjacent the membrane, and the two patents referred to above utilize hemispherical enlargements.

To increase the capacity of the pipetting device without using greater than about an eight millimeter center-to-center spacing on the tubes of the pipetting device, this invention provides for axially elongating each of these enlargements. In order to do this, the hemispherical enlargements of the prior art must not be used. Although various elongated shapes can be utilized, it is preferred to make each of the enlargements in the form of a paraboloid of revolution which progressively widens as it extends toward the membrane. A paraboloid is preferred because it has been found that this is the configuration into which the membrane inherently deflects when it is constrained in an annular region. Thus, the cavity is made geometrically compatible with the configuration into which the membrane inherently conforms to thereby reduce wear on the membrane. With this construction, each of the enlargements can have a volume of, for example, one hundred microliters or more thereby giving each tube a total capacity of about 200 microliters.

Structurally, the housing can advantageously include several plates suitably interconnected with the tubes being attached to the housing by a mounting plate. The housing is mounted on a supporting structure and a platform adapted to carry one of the trays is mounted beneath the tubes. Either or both of the platform and the housing are mounted for movement to place the lower ends of the tubes into the cavities of the tray supported by the platform. This facilitates the insertion and withdrawal of the tubes into the cavities.

The invention, together with further features and advantages thereof, may best be understood by reference to the following description taken in connection with the accompanying illustrative drawing.

DESCRIPTION OF THE PREFERRED EMBODIMENT

Figure 1:
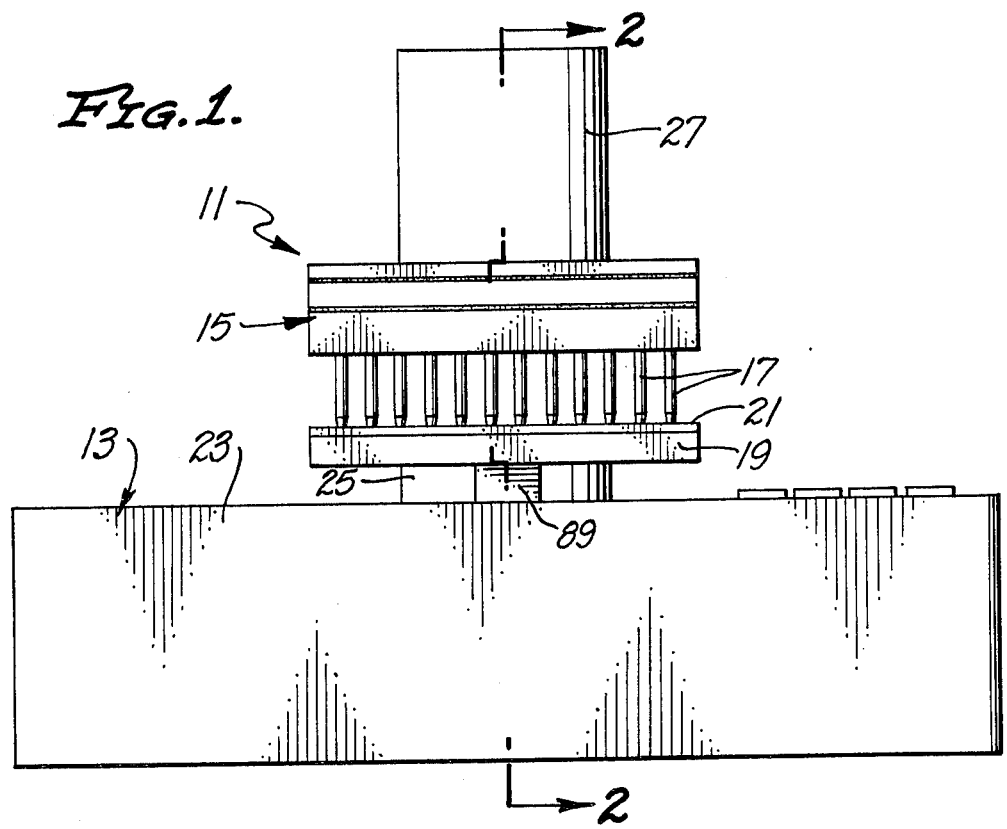
FIG. 1 is a front elevational view of a pipetting device constructed in accordance with the teachings of this invention.
Figure 2:
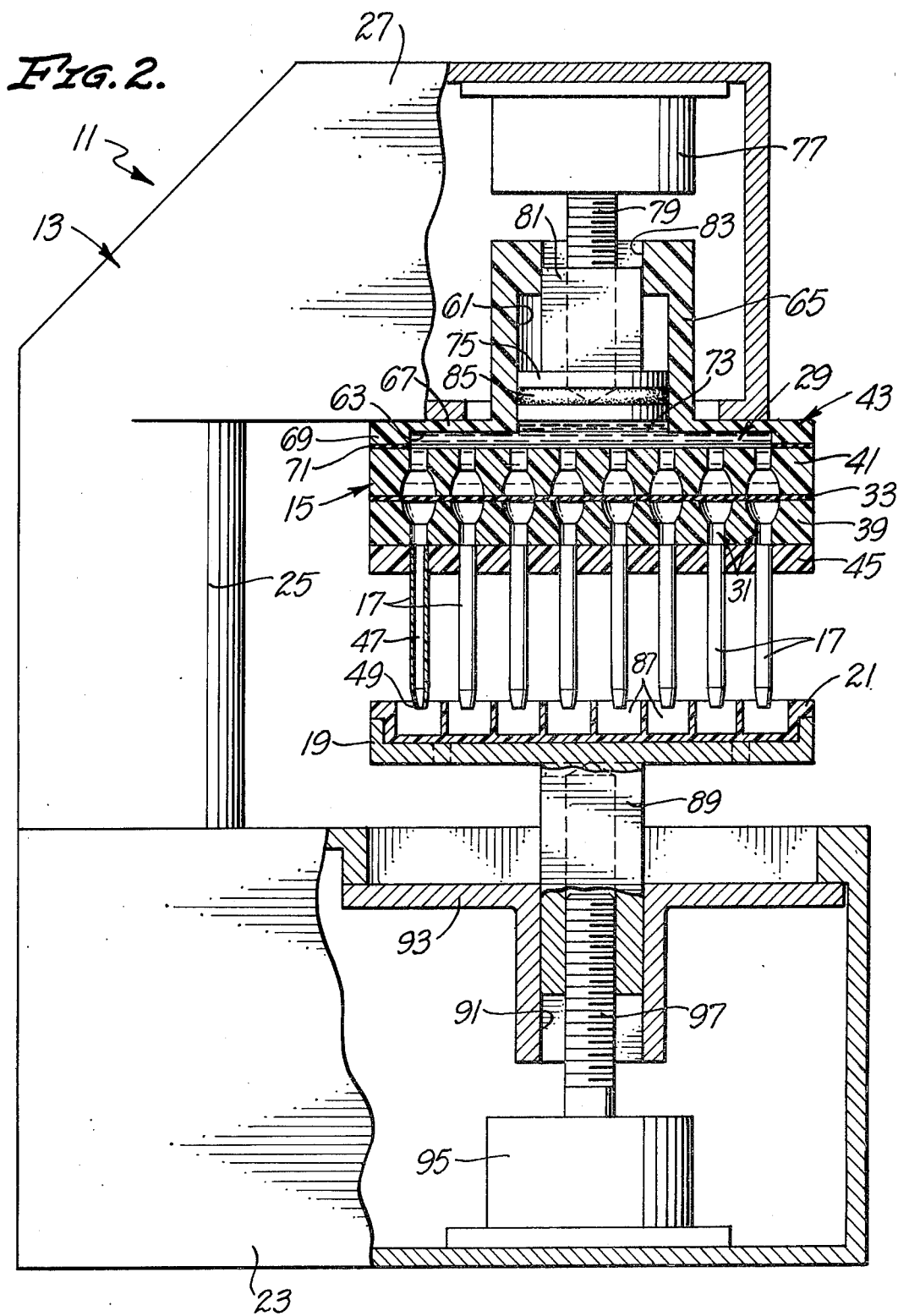
FIG. 2 is an enlarged sectional view taken generally along line 2—2 of FIG. 1.

FIGS. 1 and 2 show a pipetting device 11 which generally includes a supporting structure 13, a housing 15 mounted on the supporting structure, a plurality of tubes 17 mounted on the housing, and a platform 19 mounted on the supporting structure and adapted to carry a tray 21. The supporting structure 13 can be of various different configurations so long as it appropriately mounts the housing 15 above the platform 19. In the embodiment illustrated, the supporting structure 13 includes a base section 23, a riser section 25, and an overhead section 27 with the overhead section being spaced vertically above the top of the base section. The supporting structure 13 can be constructed of any suitable rigid materials such as plastic or metal.

Figure 3:
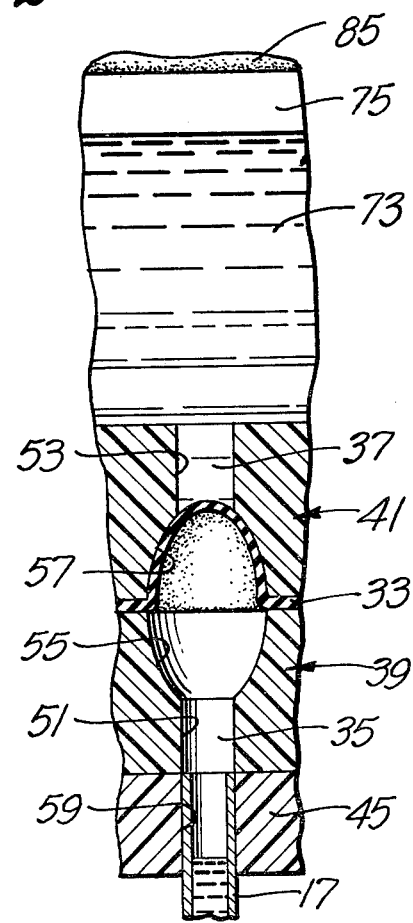
FIG. 3 is an enlarged, fragmentary sectional view of a portion of the pipetting device.

The housing 15 has a manifold chamber 29 and a plurality of passages 31 leading from the tubes 17, respectively, to the manifold chamber. A flexible impervious membrane 33 extends across the passages 31 to divide each of the passages into a first or lower passage section 35 and a second or upper passage section 37 (FIG. 3). The membrane 33 is constructed of a flexible resilient sheet of a suitable plastic or rubber.

The lower passage sections 35 provide communication, respectively, between the tubes 17 and first locations on the lower face of the membrane 33. The upper passage sections 37 extend, respectively, from second locations on the upper face of the membrane 33 to the manifold chamber 29. In this embodiment of the invention, the passage sections 35 are identical and the passage sections 37 are also identical.

Although the housing 15 could be constructed in different ways, in the embodiment illustrated, it includes a lower housing section 39 and an upper housing section 41. Each of the housing sections 39 and 41 is of platelike construction. The housing sections 39 and 41 confront each other and the membrane 33 is sandwiched therebetween and forms a seal between the housing section and also forms a seal between the passages 31. The housing 15 also includes a manifold section 43 and a mounting plate 45 for attaching the tubes 17 to the housing 15. The housing sections 39 and 41, the manifold section 43 and the mounting plate 45 are constructed of metal or a suitable plastic material and are suitably joined together as by threaded fasteners (not shown).

The tubes 17 are identical and each of them has an axial passage 47 extending therethrough. Preferably to increase accuracy, the lower end of each of the tubes has an inwardly tapered portion 49 to significantly reduce the diameter of the passage 47. For example, the diameter of the passage 47 at the tapered portion 49 may be 0.5 millimeter or less.

One of the passages 31 is provided for each of the tubes 17. Although the passages 31 can be formed in various different ways, in the embodiment illustrated, each of them includes coaxial cylindrical bores 51 and 53 (FIG. 3) of equal diameters in the housing sections 39 and 41, respectively. In addition, the passage 31 includes axially elongated radial enlargements 55 and 57 (FIG. 3) arranged coaxially with the bores 51 and 53 and provided in the housing sections 39 and 41, respectively. The enlargements 55 and 57 have greater radial demensions than the bores 51 and 53. In the embodiment illustrated, each of the enlargements 57 is in the form of identical paraboloids which are oriented to widen as they extend toward the membrane 33. The outer ends of the parabolic enlargements 55 and 57 terminate respectively in the bores 51 and 53.

Each of the parabolic enlargements 55 and 57 is axially elongated and may be about 100 microliters in volume. If it is desired to transfer 200 microliters of liquid per tube 17, it may be necessary or desirable to make each enlargement 55 and 57 slightly larger than 100 microliters to take into account the volume taken up by the membrane 33 when the latter is deflected into one of the enlargements. Alternatively, in some cases a transfer of 200 microliters is obtainable with the enlargements 55 and 57 of slightly less than 100 microliters as where the gap between the passage sections 35 and 37 created by the membrane 33 is relatively large. In either case the enlargements 55 and 57 may be considered as about 100 microliters in volume.

In the embodiment illustrated, each of the tubes 17 extends completely through a bore 59 (FIG. 3) in the mounting plate 45, and consequently, the passage 31 may be considered as terminating at the lower face of the lower housing section 39. However, if the upper end of the tube 17 is moved downwardly from the position shown in FIG. 3, then the passage 31 may be considered to include the portion of the bore 59 leading to the upper end of the tube 17.

The manifold chamber 29 includes a cylinder 61 and a connecting passage 63 for providing communication between the upper ends of the passages 31 and the cylinder. Although the cylinder 61 and the connecting passages 63 can be formed in different ways, in the embodiment illustrated, they are formed by appropriately configuring the manifold section 43 to include a cylindrical section 65, a radial wall 67 and a short axial wall 69. An annular seal 71 seals the interface between the manifold section 43 and the upper housing section 41.

A substantially incompressible flowable material 73, which is preferrably a liquid such as glycerine, fills the upper passage section 37 and the manifold chamber 29. The flowable material 73 is preferably substantially devoid of bubbles or other gaseous compenents which would tend to make the flowable material somewhat compressible. Means is provided for moving the flowable material 73 to deflect the membrane 33 in opposite directions in the passages 31 so that liquid can be drawn into and expelled from the lower ends of the tubes 17. Although such means can be provided in different ways, in the embodiment illustrated, it includes a piston 75 in the cylinder 61. In order to move the flowable material 73, means is provided for moving the piston 75 relative to the housing 15. Although this could be accomplished in different ways, in the embodiment illustrated, it is accomplished by suitably affixing and mounting the housing 15 to the lower face of the riser 25 and by moving the piston 75 relative to the housing. With this construction the manifold chamber 29 is the region within the manifold section 43 below the piston 75.

The piston 75 can advantageously be moved predetermined amounts axially within the cylinder 61 by stepping motor 77 with each "step" of the stepping motor 77 corresponding to a predetermined amount of axial movement of the piston in the cylinder and with the direction of such step controlling the direction of axial movement of the piston. To accomplish this, a stepping motor 77 rotates a screw 79, and the screw 79 is received within the piston 75. To prevent the piston 75 from rotating with the screw 79, this piston has a section 81 of square or other noncircular cross sectional configuration, and the section 81 passes through a substantially identically configured bore 83 which is in the upper end of the manifold section 43 and which has a substantially identical noncircular cross section. With this arrangement, downward movement of the piston 75 as viewed in FIG. 2 forces the flowable material 73 downwardly against the flexible membrane 33 to deflect the membrane downwardly into the paraboloids 55 and upward movement of the piston moves the flowable material upwardly to resiliently deflect the membrane 33 upwardly toward the configuration shown in FIG. 3. To prevent leakage of the flowable material across the piston 75, the piston carries an annular seal 85.

The tray 21 has a plurality of cavities 87 each of which is adapted to carry a liquid which is transferred to these cavities by the pipetting device 11. The tray 21 typically comes in two standard sizes, one of which contains twelve rows of eight cavities 87 on seven millimeter center-to-center spacing. The other size has eleven rows of ten cavities with eight millimeter center-to-center spacing. The number and positions of the tubes 17 correspond to the number and position of the cavities 87 so that one of the tubes 17 is provided for each of the cavities. For some applications, a ten millimeter center-to-center spacing of the tubes 47 is desired.

The tray 21 is supported on the platform 19. It is necessary to be able to position the lower ends of the tubes 17 into the cavities 87 so that liquid can be expelled from the cavities into the tubes. In the embodiment illustrated, this is accomplished by mounting the platform 19 on the base section 23 for vertical movement toward and away from the lower ends of the tube 17. To accomplish this, a nut 89 (FIG. 2) of noncircular cross section is attached to or integral with the lower face of the platform 19 and extends into an opening 91 of substantially identical noncircular cross sectional configuration. The opening 91 is formed in a mounting plate 93 which forms a portion of the base section 23. A stepping motor 95 is mounted on and within the base section 23 and is arranged to rotate a screw 95 which is received within the nut 89. Accordingly, rotation of the screw 97 moves the platform 19, and hence the tray 21, vertically.

To use the pipetting device 11, the motor 95 is operated to move the platform 19 up so that the lower ends of the tubes 17 are within the liquid in a receptacle or tray on the platform 19. The receptacle may be identical to the tray 21, except that it may contain a reduced number of the cavities 87 so that two or more tubes 17 extend into one cavity. The stepping motor 77 is energized for a predetermined number of steps to move the piston 75 and the flowable material 73 upwardly thereby drawing the membrane 33 upwardly into the parabolic enlargements 57 as shown in FIG. 3. Each step taken by the motor 75 corresponds to predetermined increments of movement of the piston 75 and the membrane 33. The amount that the membrane 33 is deflected upwardly determines the quantity of liquid which is drawn into each of the tubes 17. Consequently, the volume of liquid drawn into each of the tubes 17 is in turn directly proportional to the number of steps taken by the stepping motor 77. In the embodiment illustrated, the membrane 33 is fully extended upwardly so that it neatly conforms to the parabolic configuration of the enlargements 57. Consequently, approximately one hundred microliters of liquid are drawn into each of the tubes 17. The membrane 33 separates the flowable material 73 from the air below the membrane.

If it is desired to draw in more than one hundred microliters per tube, the stepping motor 77 first moves the piston 75 downwardly to force the flowable material downwardly to deflect the membrane 33 into the lower parabolic enlargements 55, and thereafter the piston is moved upwardly. Thus, the number of steps taken by the motor 77 in moving the piston 75 upwardly controls the volume of liquid drawn into each of the tubes 17.

After the desired amount of liquid has been removed from the receptacle, the platform 19 is lowered and the tray 21 is placed on the platform. The platform 19 is then raised to place the lower ends of the tubes within the cavities of the tray 21, and the piston 75 is moved downwardly to expel the liquid from the tubes 17. In this manner, accurate quantities of liquid can be rapidly transferred from the cavities of one tray to the cavities of a second tray.

Various state of the art methods may be used to control the motor 77 and 95. For example, the motor 95 can be turned on and off manually or with limit switches to move the platform 19 to the desired elevation. Similarly, the stepping motor 77 can be manually set to take any desired number of steps in either direction.

Although an exemplary embodiment of the invention has been shown and described, many changes, modifications and substitutions may be made by one having ordinary skill in the art without necessarily departing from the spirit and scope of this invention.

We claim:

1. A pipetting device comprising:
   a housing;
   a plurality of tubes mounted on said housing, each of said tubes having a passage extending therethrough;
   said housing having a manifold chamber and a plurality of passages leading from said tubes, respectively, to said manifold chamber;
   flexible impervious membrane means extending across said passages to divide each of said passages into a first passage section and a second passage section, said first passage sections providing communication respectively between said tubes and first locations on one side of said membrane means, said second passage sections extending respectively from second locations on the other side of said membrane means to said manifold chamber, said second locations being opposite said first locations, respectively;

a substantially incompressible flowable material filling said second passage and said manifold chamber, said flowable material being a liquid; and means for moving the flowable material to deflect the membrane means in opposite directions in said passages whereby liquid can be drawn into and expelled from said tubes.

2. A pipetting device as defined in claim 1 wherein said moving means includes means for selectively moving the flowable material variable amounts to thereby vary the deflection of the membrane means whereby the amount of liquid drawn into and expelled from said tubes can be varied.

3. A pipetting device as defined in claim 1 including a supporting structure, means for mounting said housing on said supporting structure, a platform, means for mounting said platform on said supporting structure beneath said housing and means for moving at least one of said housing and said platform so that the spacing between the tubes and the platform can be varied.

4. A pipetting device as defined in claim 1 wherein said manifold chamber includes a cylinder, said moving means includes a piston in said cylinder for pumping the flowable material, and means for moving the piston to any one of a plurality of positions in said cylinder to thereby control and vary the deflection of the membrane means whereby the amount of liquid drawn into and expelled from said tubes can be varied.

5. A pipetting device as defined in claim 4 wherein said piston moving means includes a stepping motor for moving the piston whereby each step of said motor corresponds to a predetermined volume of liquid drawn into or expelled from said tubes.

6. A pipetting device as defined in claim 1 wherein at least some of the passage sections have radial enlargements adjacent the membrane means and each of said enlargements is axially elongated.

7. A pipetting device as defined in claim 6 wherein at least some of the enlargements are paraboloids of revolution which are oriented to generally widen as they extend toward said membrane means.

8. A pipetting device as defined in claim 6 wherein the center-to-center spacing of said tubes is no more than about eight millimeters and the volume of each of said enlargements is no less than about 100 microliters.

* * * * *